United States Patent [19]

Hashimoto et al.

[11] 3,971,651
[45] July 27, 1976

[54] PLANT GROWTH MODIFIER AND A PROCESS FOR PREPARATION THEREOF

[75] Inventors: Tohru Hashimoto, Musashino; Akira Kawarada; Sachiko Tamura, both of Tokyo, all of Japan

[73] Assignee: Rikagaku Kenkyusho, Japan

[22] Filed: Apr. 22, 1975

[21] Appl. No.: 570,960

Related U.S. Application Data

[62] Division of Ser. No. 331,498, Feb. 12, 1973, Pat. No. 3,917,477.

[52] U.S. Cl. .................................. 71/122; 71/123; 71/124; 71/126; 71/127
[51] Int. Cl.[2] .......................................... A01N 9/24
[58] Field of Search ............. 71/124, 122, 123, 126, 71/127

[56] References Cited
OTHER PUBLICATIONS

Hashimoto et al., Chem. Abst., vol. 80, (1974), 117165a.
Bradsher et al., Chem. Abst., vol. 49, (1955), 8202i.

*Primary Examiner*—Lewis Gotts
*Assistant Examiner*—Catherine L. Mills

[57] ABSTRACT

A plant growth modifier comprising as an active ingredient at least one compound selected from the group consisting of compounds (I), (II) and (III) expressed by the following formulae:

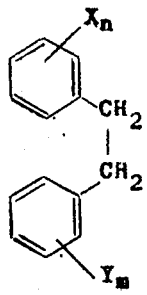
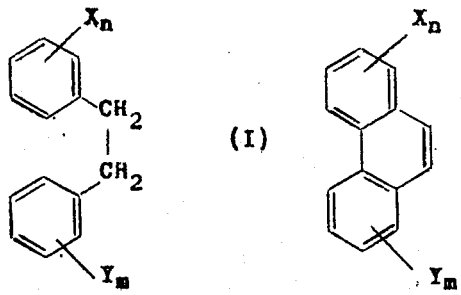

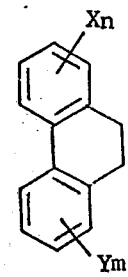

wherein X and Y stand for a member selected from Cl—, HO—, $CH_3O$— and $CH_3CO$— and $n$ and $m$ stand for an integer of 0 to 3.

6 Claims, No Drawings

PLANT GROWTH MODIFIER AND A PROCESS FOR PREPARATION THEREOF

This is a division of application Ser. No. 331,498 filed Feb. 12, 1973, now U.S. Pat. No. 3,917,447.

The present invention relates to a novel growth modifier for plants. Particularly the present invention relates to a novel plant growth modifier useful for controlling growth and germination of seeds, sprouting or budding of plants, for recuring ill plants, and for regulating dormant stage of seeds, tubers, corms, bulbs and buds.

Various research works have heretofore been made on plant growth modifiers, and a great number of compounds have been proposed as plant growth modifiers, such as maleic hydrazide, abscisic acid, AMO-1618, Phosphon-D, B-Nine, etc. Further, it is known that irradiation with γ-ray is effective for artificially prolonging the dormant stage. However, none of plant growth modifiers comprising active ingredients such as claimed in this invention have heretofore been known in the art.

We have made extensive research with a view to providing novel plant growth controlling agents and found that compounds expressed by the following general formulae (I), (II) and (III) are highly effective for modifying growth of plants and inducing or prolonging the dormancy in plants. Based on the foregoing finding, we have now completed plant growth modifiers of this invention.

Therefore the present invention relates to a plant growth modifier comprising as an active ingredient at least one compound selected from the group consisting of compounds (I), (II) and (III) expressed by the following formulae:

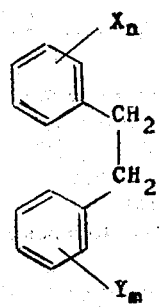

(I)

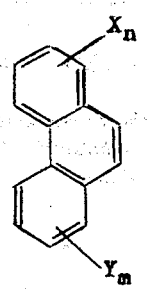

(II)

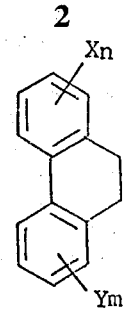

(III)

wherein X and Y stand for a member selected from Cl—, HO—, $CH_3O$— and $CH_3CO$— and n and m stand for an integer of 0 to 3.

Plant growth modifiers of this invention make it possible to artificially modify the intrinsic habitudes of various plants. For instance, they can control the budding of plants or excessive growth of plants in growing period, and they make it possible to dwarf plants in a healthy state. Further, if seeds, tubers, bulbs and buds lying dormant are treated with the plant growth modifiers of this invention, the period of the dormant stage thereof can be preferably prolonged, and if they are treated when they are going to initiate growth, it is possible to drive them into dormancy again. Thus, the active ingredient of this invention can be applied at a suitable concentration according to an appropriate method and it is possible to modify or retard the growth and germination in various plants. For instance, when the plant growth modifier of this invention is applied to growing plants such as chrysanthemums, dahlias, begonias, cosmoses and the like, the elongation of stalks is suppressed in the healthy state to give dawf plants, whereby the appreciation value of these plants can be increased. Further, when the plant growth modifier of this invention is applied to rice plants, wheat plants and the like, excessive growth of halm is inhibited and a tendency of these plants to fall down on earth when they come into ears can be reduced, whereby either the crop or quality of the crops can be greatly improved. Moreover, when corms, bulbs or tubers of onion, garlic, potato, tulip and the like are treated with the plant growth modifier of this invention, the period of the dormant or resting stage can be prolonged to maintain freshness in these plants for a long time and increase values as foods or seeds. In addition, if mulberry trees are treated with the modifier of this invention when late frosting threatens to come before the initiation of germination, they can be prevented from damage by the frost. Thus various advantages can be obtained by application of the plant growth modifiers of this invention.

Compounds expressed by the above general formulae (I), (II) and (III) which are used as active ingredients of plant growth modifiers of this invention will now be illustrated. These compounds (I), (II) and (III) are respectively bibenzyl, phenanthrene and dihydrophenanthrene compounds which may optionally have such substituents as Cl—, HO—, $CH_3O$— and $CH_3CO$—. These compounds are prepared from benzaldehyde and phenyl-acetic acid or their substituted derivatives, and a variety of bibenzyl, and phenanthrene compounds can be obtained depending on the kind of substituents bonded to such starting compounds.

Methods of preparing these compounds (I), (II) and (III) will now be illustrated by reference to hydroxymethoxy-bibenzyl as a typical instance of the compound (I), hydroxy-methoxy-phenanthrene as a typical instance of the compound (II) and hydroxy-methoxy- 9,10-dihydrophenanthrene as a typical instance of the compound (III).

Hydroxybenzaldehyde is mixed with methoxyphenylacetic acid and the resulting mixture is reacted with acetic anhydride and trimethylamine, to obtain α-methoxyphenyl-hydroxy-cinnamic acid. When this compound is acetylated by heating in a nitrogen gas atmosphere in the presence of quinoline and copper chromite, acetoxy-methoxy-stilbene is formed. Then, this stilbene derivative is catalytically reduced and hydrolyzed with an alkali to obtain 3-hydroxy-5 -methoxybibenzyl.

By similar procedures there may readily be obtained bibenzyl compounds such as 2,2'-dihydroxy-3,5-dimethoxybibenzyl, 3,4'-dihydroxy-4,5-dimethoxybibenzyl, 4,6-dihydroxy-3-acetylbibenzyl, 2,4-dihydroxybibenzyl, 3,5,3',5'-tetrachloro-2,2'-dihydroxybibenzyl, 3,3',5'-trihydroxy-4-methoxybibenzyl, 3,3'-dihydroxy-5-methoxybibenzyl, etc.

Methods of preparing phenanthrenes expressed by the above general formulae (II) and (III) will now be described. Acetoxy-methoxy-stilbene mentioned above with respect to the preparation of compounds (I) is dissolved in ethanol, and iodine is added to the solution. When the resulting solution is irradiated, the ring-closure is caused to occur by the photo-chemical reaction and acetoxymethoxy-phenanthrene is formed. Hydrolysis of this compound gives hydroxy-methoxy-phenanthrene. When this compound is catalytically reduced, hydroxy-methoxy-9,10-dihydrophenanthrene is obtained.

By similar procedures there can easily be obtained 2,4-dimethoxy-6-hydroxyphenanthrene, 4-hydroxy-2,6,7-trimethoxyphenanthrene, 2,6-dihydroxy-3,4,7-trimethoxyphenanthrene, 4,6,7-trihydroxy-2,3-dimethoxyphenanthrene, 2,4-dimethoxy-6-hydroxyphenanthrene, 6-chloro-9-acetylphenanthrene, 7-hydroxy-2,6-diacetyl-9,10-dihydrophenanthrene, 2,3,5,7-tetrahydroxy-9,10-dihydrophenanthrene, 4,7-dihydroxy-2,3,6-trimethoxy-9,10-dihydrophenanthrene, 4,7-dihydroxy-2,6-dimethoxy-9,10-dihydrophenanthrene, etc.

Among compounds exemplified above, 2,2'-dihydroxy-3,5-dimethoxybibenzyl and 3,3'-dihydroxy-5-methoxy-bibenzyl are novel substances heretofore unknown in the art. Alternately, these compounds can be isolated from natural sources, for instance from a subterranean or terrestrial tubers of yam (*Dioscorea batatas Decne.*) or other organs in the dormant stage. An example of the method of obtaining these novel compounds will be described below.

The terrestrial tubers of yam (*Discorea batatas Decne.*) is immersed in an organic solvent such as methanol, ethanol and acetone or ground together with such solvent, to recover extract. The extract is concentrated under reduced or atmospheric pressure to remove the solvent used for extraction. Instead of the above organic solvent, water incorporated with 0.05 – 0.1% of Tween 20 or Tween 80 (surfactant manufactured by Atlas Chemical Co., U.S.A.) can be used as an extraction solvent. The resulting extract, as it is or after adjust pH to 6.5 – 8.0, is shaken with ethyl ether, isopropyl ether, ethyl acetate, butyl acetate, butyl alcohol, amyl acohol or benzene, and the shaken liquor is allowed to stand still. When the liquor is separated into two layers, the upper layer is collected. This procedure is repeated twice or three times, and the collected upper layers are combined. The combined liquor is concentrated to obtain an oily impure substance. This impure substance is purified to colorless crystals by the following column adsorption chromatography.

Silica gel having a size of 70 – 325 mesh is packed in a column by the use of benzene, and the above oily impure substance is adsorbed on top of the silica gel column, and then eluted with ethyl acetate-containing benzene while increasing the ethyl acetate concentration gradually. Thus, colorless needle crystals of 2,2'-dihydroxy-3,5-dimethoxybibenzyl and 3,3'-dihydroxy-5-methoxybibenzyl can be obtained at ethyl acetate concentrations of 3 – 4% and 6 – 10%, respectively.

Instead of silica gel, there may be employed alumina, magnesia and the like as a column filler. Such mixed solvents as benzene-methanol, benzene-ethanol, chloroform-ethyl acetate, chloroform-methanol and chloroform-ethanol can be used as eluting solvents as well as benzene-ethyl acetate.

In addition to the above-mentioned column adsorption chromatography, it is possible to employ effectively the partition column chromatography in which silica gel or Sephadex is used as a support of the stationary phase. In this case, the lower layer of a n-hexane-methanol (1 : 1 volume ratio) or n-hexane-ethyl acetate-methanol-water (2 : 2 : 2 : 1 volume ratio) mixture is used as the stationary phase and the upper layer thereof is used as the mobile phase, and thus the developing elution is conducted.

We have designated the above two novel compounds inclusively as "batatasin," of which physical and chemical properties are as follows:

2,2'-Dihydroxy-3,5-dimethoxybibenzyl

1. Molecular weight: 274
2. Molecular formula: $C_{16}H_{18}O_4$
3. Melting point: 48 – 50°C
4. Ultraviolet absorption spectrum:

| Maximum absorption (mm) | Molecular absorbance |
| --- | --- |
| 282 (shoulder) | $\epsilon : 3.07 \times 10^3$ |
| 275 | $\epsilon : 3.70 \times 10^3$ |
| 210 | $\epsilon : 3.95 \times 10^4$ |

5. Infrared absorption spectrum:
    Maximum absorption, $cm^{-1}$
    3400, 2940, 2840, 1596, 1514, 1458, 1432, 1358, 1236, 1204, 1170, 1141, 1095, 1046, 996, 830, 755

6. Nuclear magnetic resonance spectrum:

| δ value in heavy chloroform | | |
| --- | --- | --- |
| 7.06 | 2H | multiplet |
| 6.90 | 1H | quadruplet |
| 6.76 | 1H | quadruplet |
| 6.49 | 1H | doublet |
| 6.24 | 1H | doublet |
| 5.70 | 1H | singlet |
| 4.60 | 1H | singlet |
| 3.87 | 3H | singlet |
| 3.79 | 3H | singlet |
| 2.85 | 4H | singlet |

7. Crystal form: colorless needles
8. Solubility:
    Soluble in ordinary solvents such as ethanol, acetone, ethyl acetate and ether, but insoluble in hexane and water.
9. Color reaction:

Negative to 2,4-dinitrophenyl hydrazine but exhibiting a scarlet color to vanillin.
10. Rf value:
    0.44 (measured by silica gel thin layer chromatography employing chloroform/acetic acid of 95/5 volume ratio)

3,3'-Dihydroxy-5-methoxybibenzyl
1. Molecular weight:244.1
2. Molecular formula:$C_{15}H_{16}O_3$
3. Melting point:93.5° – 94.5°C
4. Ultraviolet spectrum:
    In ethanol
        Spectral characteristics under neutral and hydrochloric acid-acidifying conditions are as follows:

| Maximum adsorption (mm) | Molecular absorbance |
|---|---|
| 281 | $\epsilon : 0.32 \times 10^4$ |
| 276 | $\epsilon : 0.34 \times 10^4$ |
| 223 | $\epsilon : 1.29 \times 10^4$ |

Spectral characteristics under alkaline conditions with addition of KOH of 0.005 N are as follows:

| Maximum adsorption (mm) | Molecular absorbance |
|---|---|
| 292 | $\epsilon : 0.46 \times 10^4$ |
| 283 (shoulder) | $\epsilon : 0.42 \times 10^4$ |

5. Infrared adsorption spectrum:
    Maximum adsorption, $cm^{-1}$
    3340, 1620, 1600, 1450, 1190, 1150, 1055, 980, 940, 690
6. Nuclear magnetic resonance spectrum:

| $\delta$ value in heavy chloroform | |
|---|---|
| 7.14 | triplet |
| 6.78 | singlet |
| 6.66 | multiplet |
| 6.26 | multiplet |
| 3.74 | singlet |
| 2.82 | singlet |

7. Crystal form: colorless needles
8. Solubility:
    Soluble in ordinary solvents such as ethanol, acetone, ethyl acetate and ether, but difficultly soluble in water and insoluble in hexane.
9. Color reaction:
    Negative to 2,4-dinitrophenyl hydrazine but exhibiting an orange red color to vanillin.
10. Rf value:
    0.20 (measured by silica gel thin layer chromatography using chloroform/acetic acid of 95/5 volume ratio)
    This novel substance, batatasin, exhibits a very high effect of controlling the growth of germination in plants. Therefore, the activity of this substance can be detected by the biological test as follows:
    Buds of terrestrial tuber of a yam (Dioscorea batatas Decne.) or that of a subterranean tuber of a potato which have awakened from hibernation are cut out in the cylindrical form by means of a cork borer. A filter paper or absorbent cotton containing an aqueous solution of a sample to be tested is placed in a culture dish, and the cut-out buts are arranged on the filter paper or absorbent cotton. Cultivation is carried out in this state at about 25°C for 1 – 2 weeks, and the degree of inhibition of germination is observed.
    Alternately, it is possible to examine by a method comprising sowing seeds of a lettuce (Lactuca sativa L.) or a rice plant on a culture dish arranged in the same manner as described above, conducting cultivation at 23°C for 2 – 3 days and observing the germination state. Moreover, it is possible to examine by a way wherein seeds of oats (Avena sativa L.) are allowed to germinate under weak red light, and three days after sowing, a section of 5 mm in length is cut from a coleoptile of about 25 mm in length. Sections thus prepared are floated on a culture medium prepared by dissolving a sample to be tested in an aqueous solution containing 0.1 mg/l of indoleacetic acid, 0.05% of Tween 20 and 2% of sucrose. Cultivation is continued for 18 hours at 25°C in the dark. Then, the detection can be made based on inhibition of growth of the coleoptile sections.
    Further a chemical detection method, which utilize a color reaction with vanillin-sulfuric acid can be used. According to this method, a sample to be tested is placed in a thin layer plate of Silica Gel G (product of Merk Co.) and is developed with chloroform-acetic acid (95/5 volume ratio). Then a vanillin-sulfuric acid reagent is sprayed to the sample and the plate is heated at 110°C for about 5 minutes. Thus, the above novel substances are detected as scarlet and orange red spots, respectively.
    As decribed above, the plant growth modifier of this invention comprises at least one compound selected from the group consisting of compounds expressed by the above general formulae (I), (II) and (III). These active ingredient compounds can be applied directly as they are. Still further, they can be applied in the form of various formulations adopted in the agricultural field. For instance, they are formed into various agricultural formulations such as dusts, wettable powders, emulsions and granules by blending with solid or liquid carriers, diluents, developers, dispersants and other adjuvants. Further, they exhibit their activities at any concentration or application rate varying in very broad range. Therefore, the concentration and application rate can be selected and decided appropriately depending on the object of application.
    Moreover, the plant growth modifier of this invention can be used in combination with other plant growth modifiers, fungicides, insecticides or fertilizers according to need, whereby a variety of agricultural application can be attained.
    This invention will now be illustrated by reference to Examples showing the preparation of agricultural formulations and the utility of the plant growth modifier of this invention, but this invention is not limited to these Examples. In Examples all of "parts" are on a weight basis.

EXAMPLE 1

0.02 part of 3-hydroxy-5-methoxybibenzyl was mixed with 99.98 parts of clay, and the mixture was ground to obtain dusts.

EXAMPLE 2

2 parts of 2,4-dimethoxy-6-hydroxyphenanthrene, 20 parts of Tween 20 (surfactant manufactured by Atlas Chemical Co., U.S.A), 30 parts of acetone and 48 parts of water were mixed together to obtain a wettable powder.

EXAMPLE 3

2 parts of 7-hydroxy-2,6-diacetyl-9,10-dihydrophenanthrene, 4 parts of glycol ether and 94 parts of methanol were mixed together to obtain an emulsifiable liquor.

The utility of the plant growth modifier of this invention will be illustrated below.

EXAMPLE 4

A compound illustrated in Table 1 was dissolved in dimethylformamide and the solution was diluted to desired concentrations with water containing 2% of sucrose. In control test dimethylformamide was applied in the same amount as that of treated groups. This solvent gives no phytotoxicity to plants to be tested if the content in water is 1% or less. The prepared liquors were poured into culture dishes of 3 cm diameter, the amount of the medium poured into one dish being 2 ml. Sections of 5 mm in length cut from a coleoptiles of oats (*Avena sativa L.*) which have been grown in the dark were floated on the test media in the culture dishes and cultured at 25°C for 20 hours in the dark to determine the growth-inhibition degrees. Results are shown in Table 1.

In the control group, the coleoptile elongated by about 5 mm during the experiment.

Table 1

| Compound No. | Active Ingredient | Melting Point(°C) | Growth Inhibition in oats coleoptile (concentration giving 50% inhibition (μg/ml) |
|---|---|---|---|
| 1 | 3-hydroxy-5-methoxybibenzyl | 50–52 | 80 |
| 2 | 2,2'-dihydroxy-3,5-dimethoxybibenzyl | 48–50 | 100 |
| 3 | 3,4'-dihydroxy-4,5-dimethoxybibenzyl | 128–130 | 150 |
| 4 | 4,6-dihydroxy-3-acetyldibenzyl | 136 | 90 |
| 5 | 2,4-dihydroxybibenzyl | 137–138 | 110 |
| 6 | 3,5,3',5'-tetrachloro-2,2'-dihydroxybibenzyl | 203–204 | 30 |
| 7 | 3,3',5'-trihydroxy-4-methoxybibenzyl | 135–136 | 75 |
| 8 | 3,3'-dihydroxy-5-methoxybibenzyl | 93.5–94.5 | 100 |
| 9 | 2,4-dimethoxy-6-hydroxyphenanthrene | 135 | 130 |
| 10 | 4-hydroxy-2,6,7-trimethoxyphenanthrene | 148–149 | 90 |
| 11 | 2,6-dihydroxy-3,4,7-trimethoxyphenanthrene | 297–300 | 100 |
| 12 | 4,6,7-trihydroxy-2,3-dimethoxyphenanthrene | 155–156 | 120 |
| 13 | 2,4-dimethoxy-6-hydroxyphenanthrene | 135 | 90 |
| 14 | 6-chloro-9-acetylphenanthrene | 139–140 | 70 |
| 15 | 7-hydroxy-2,6-diacetyl-9,10-dihydrophenanthrene | 155 | 130 |
| 16 | 2,3,5,7-tetrahydroxy-9,10-dihydrophenanthrene | 291–292 | 150 |
| 17 | 4,7-dihydroxy-2,3,6-trimethoxy-9,10-dihydrophenanthrene | 147–150 | 200 |
| 18 | 4,7-dihydroxy-2,6-dimethoxy-9,10-dihydrophenanthrene | 128–130 | 180 |

EXAMPLE 5

Every compound shown in Table 1 was respectively dissolved at various concentrations in distilled water containing 1% of dimethylformamide, and 3 ml each of the resulting solutions was poured into a culture dish of 6 cm diameter in which 2 filter papers were spread. About 100 seeds (non-dormant ware head seeds) of lettuce (*Lactuca sativa L.*) were shown in each dish, and they were allowed to stand at 23°C in the dark for 2 days. Germination percentages were determined and plotted against the concentrations of the compound tested. From the graphs obtained the concentration to give 50% inhibition was determined. The definition of inhibition rate is given in the following formula:

$$\frac{\text{germination percentage of treated lot}}{\text{germination percentage of control lot}}$$

Usually the germination percentage of the untreated control lot was about 95%. Results are shown in Table 2.

Table 2

Inhibition of Germination of Lettuce Seeds

| Compound No. | Concentration (μg/ml) Giving 50% Inhibition |
|---|---|
| 1 | 60 |
| 2 | 100 |
| 3 | 120 |
| 4 | 90 |
| 5 | 90 |
| 6 | 10 |
| 7 | 75 |
| 8 | 80 |
| 9 | 100 |
| 10 | 60 |
| 11 | 100 |
| 12 | 140 |
| 13 | 80 |
| 14 | 30 |
| 15 | 80 |
| 16 | 160 |
| 17 | 120 |
| 18 | 160 |

EXAMPLE 6

Bulbils (fleshy buds for breeding formed on stems) of yam (*Dioscorea batatas Decne.*) were stored at a low temperature of 5°C for 3 months and awakened from hibernation. These fleshy buds were treated with the agricultural chemical of this invention in the following manner to lead them to hibernation again.

Every active ingredient compound of this invention shown in the following Table 3 was dissolved emulsified in distilled water containing 1% of dimethylformamide and 0.05% of Tween 20. 25 ml the resulting liquor was poured into a culture dish of 9 cm diameter in which absorbent cotton was spread, and 30 of bulbis which had been subjected to the above low temperature treatment and awakened from dormancy were sown on the dish and they were allowed to sprout at 23°C under light of 1,800 luxes for 2 weeks. As a result of examination of the sprouting state, it was confirmed that the active ingredient compound of this invention exhibited, as shown in Table 3, a prominent action of inhibiting germination, i.e., a high dormancy-inducing activity.

Table 3

| Compound No. | Concentration ($\mu$g/ml) | Germination Ratio (%) |
|---|---|---|
| 8 | 300 | 50 |
| 4 | 300 | 63 |
| 3 | 300 | 42 |
| 6 | 300 | 15 |
| 13 | 300 | 60 |
| 11 | 300 | 50 |
| 10 | 300 | 45 |
| 14 | 300 | 70 |
| 17 | 300 | 40 |
| untreated control | — | 80 |

EXAMPLE 7

4-Hydroxy-2,6,7-trimethoxyphenanthrene and 3,3'-dihydroxy-5-methoxybibenzyl were respectively dissolved at various concentrations in water containing 0.05% of Tween 20, and 30 ml each of the resulting solutions were poured into culture dishes of 9 cm in diameter containing 1 g of absorbent cotton.

Thirty bulbils of yam (*Discorea batatas Decne.*) which had been awakened from dormancy were planted in each of the so arranged culture dishes, and the germination test was carried out at 23°C either in the dark or in the light. Data of the sprouting obtained after 20 days' cultivation are shown in Table 4, from which it is seen that the above two compounds exhibited a high sprouting-inhibiting activity.

Table 4

| Compound | Concentration (mg/l) | Sprouting Ratio (%) | |
|---|---|---|---|
| | | dark place | light place |
| 4-hydroxy-2,6,7-trimethoxyphenanthrene | 100 | 46 | 14 |
| same as above | 300 | 30 | 8 |
| same as above | 1000 | 23 | — |
| 3,3'-dihydroxy-5-methoxybibenzyl | 100 | 56 | 23 |
| same as above | 300 | 22 | 18 |
| same as above | 1000 | 14 | — |
| untreated control | 0 | 56 | 44 |

The inhibition of sprouting attained by the above chemical treatment was completely relieved by subjecting the tuber to a low temperature treatment at 4°C for additional one month, and no phytotoxicity was found.

EXAMPLE 8

4-Hydroxy-2,6,7-trimethoxyphenanthrene and 3,3'-dihydroxy-5-methoxybibenzyl were respectively dissolved in water containing 0.05% of Tween 20 and 1% of dimethylformamide, and each of the resulting solution was poured into a culture dish, 6 cm in diameter, in which 2 layers of filter paper were spread to form a germination bed. 100 seeds of a lettuce (*Lactuca sativa L.*) were sown on the germination bed and cultivation was conducted for 2 days at 23°C. Results of examination on the germination ratio are shown in Table 5, from which it is seen that these compounds exhibited a germination-inhibiting activity.

Germination ratio = $\dfrac{\text{The number of seeds germinated}}{\text{The number of seeds sown}}$ Table 5

| Compound | Concentration (mg/l) | Germination Ratio (%) |
|---|---|---|
| 4-hydroxy-2,6,7-trimethoxyphenanthrene | 30 | 78 |
| same as above | 100 | 43 |
| same as above | 300 | 10 |
| 3,3'-dihydroxy-5-methoxybibenzyl | 30 | 52 |
| same as above | 100 | 26 |
| same as above | 300 | 0 |
| untreated control | 0 | 90 |

Germination-inhibited seeds was not blighted but when they were washed with water and transplanted on a culture dish free of 4-hydroxy-2,6,7-trimethoxyphenanthrene or 3,3'-dihydroxy-5-methoxybibenzyl, they showed complete germination.

EXAMPLE 9

Oats (*Avena sativa L.*) were allowed to germinate under a weak red light at 25°C and 3 days after germination sections of 5 cm in length were cut from coleoptiles about 25 mm in length. 4-Hydroxy-2,6,7-trimethoxyphenanthrene or 3,3'-dihydroxy-5-methoxybibenzyl was dissolved in a culture medium comprising 0.1 mg/l of indoleacetic acid, 0.05% of Tween 20 and 2% of sucrose, the balance being water. Ten of the above cut-out coleoptile pieces were flated on the resulting culture medium and cultivation was conducted at 25°C for 18 hours to examine the growth state and the results shown in Table 6 were obtained. From the table it is seen that the above compounds exhibited a growth-inhibiting activity.

Table 6

| Compound | Concentration (mg/l) | Growth Inhibition* ratio (%) |
|---|---|---|
| 4-hydroxy-2,6,7-trimethoxyphenanthrene | 30 | 16 |
| same as above | 100 | 44 |
| 4-hydroxy-2,6,7-trimethoxyphenanthrene | 300 | 79 |
| 3,3'-dihydroxy-5-methoxybibenzyl | 30 | 39 |
| same as above | 100 | 76 |
| same as above | 300 | 84 |
| untreated control | 0 | 0 |

* Growth inhibition ratio =

$\dfrac{(\text{Length of untreated control sections}) - (\text{Length of treated sections})}{(\text{Length of untreated control sections}) - (\text{Initial length of sections})} \times 100$

EXAMPLE 10

4-Hydroxy-2,6,7-trimethoxyphenanthrene or 3,3'-dihydroxy-5-methoxybibenzyl was dissolved in acetone, and the resulting solution was placed in culture dishes in which 2 layers of filter paper were spread so as to give required amounts of the test compound. After the acetone was removed by evaporation, Hoagland's nutrient solution containing 0.05% of Tween 20 was poured into the culture dishes. Seeding of lettuce (*Lactuca sativa L.*), which had been germinated in a different place, were transplanted to the culture dishes and cultivation was carried out in a light place at 23°C for 3 days. Then, the lengths of the stems (hypocotyls) were measured to determined the growth inhibition ratio. Results are shown in Table 7.

Table 7

| Compound | Concentration (mg/l) | Growth Inhibition Ratio (%) |
|---|---|---|
| 4-hydroxy-2,6,7-tri-methoxyphenanthrene | 30 | 13 |
| same as above | 100 | 45 |
| same as above | 300 | 72 |
| 3,3'-dihydroxy-5-methoxybibenzyl | 30 | 21 |
| same as above | 100 | 48 |
| same as above | 300 | 86 |
| untreated control | 0 | 0 |

What we claim is:

1. A method for inhibiting the growth and germination of higher plants which comprises applying thereto an effective amount of a compound of the formula:

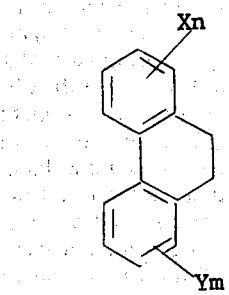

wherein X is selected from the group consisting of hydroxy, methoxy and acetyl and Y is selected from the group consisting of chloro, hydroxy, methoxy and acetyl and $m$ and $n$ are integers independently having a value of from 1 to 3.

2. The method according to claim 1, wherein the compound is in combination with a slid or liquid carrier or diluent.

3. The method according to claim 1, wherein the compound is 7-hydroxy-2,6-diacetyl-9,10-dihydrophenanthrene.

4. The method according to claim 1, wherein the compound is 2,3,5,7-tetrahydroxy-9,10-di-hydrophenanthrene.

5. The method according to claim 1, wherein the compound is 4,7-dihydroxy-2,3,6-trimethoxy-9,10-dihydrophenanthrene.

6. The method according to claim 1, wherein the compound is 4,7-dihydroxy-2,6-dimethoxy-9,10-dihydrophenanthrene.

* * * * *